(12) United States Patent
Weaver et al.

(10) Patent No.: US 8,829,886 B2
(45) Date of Patent: Sep. 9, 2014

(54) SYSTEMS AND METHODS FOR DEFECT DETECTION USING EXOELECTRONS

(75) Inventors: Stanton Earl Weaver, Broadalbin, NY (US); Joseph Darryl Michael, Delmar, NY (US)

(73) Assignee: General Electric Company, Niskayuna, NY (US)

( * ) Notice: Subject to any disclaimer, the term of this patent is extended or adjusted under 35 U.S.C. 154(b) by 377 days.

(21) Appl. No.: 13/325,731

(22) Filed: Dec. 14, 2011

(65) Prior Publication Data

US 2013/0153781 A1 Jun. 20, 2013

(51) Int. Cl.
*G01N 27/00* (2006.01)

(52) U.S. Cl.
USPC ............................................ 324/71.1; 324/96

(58) Field of Classification Search
None
See application file for complete search history.

(56) References Cited

U.S. PATENT DOCUMENTS

| | | | |
|---|---|---|---|
| 3,715,583 A | | 2/1973 | Braunlich |
| 4,089,224 A | * | 5/1978 | Scott et al. ...................... 73/587 |
| 4,160,702 A | | 7/1979 | Baxter |
| 4,654,556 A | | 3/1987 | Comby |
| 4,927,299 A | * | 5/1990 | Ramalingam et al. ......... 407/120 |
| 5,184,516 A | * | 2/1993 | Blazic et al. .................... 73/799 |
| 2010/0107765 A1 | * | 5/2010 | Murakami et al. .............. 73/587 |

FOREIGN PATENT DOCUMENTS

| | | |
|---|---|---|
| JP | 57158546 A | 9/1982 |
| JP | 59174745 A | 10/1984 |

OTHER PUBLICATIONS

Search Report and Written Opinion from corresponding PCT Application No. PCT/US2012/069535 dated Apr. 5, 2013.
Moore et al., "The Early Detection of Fatigue Damage by Exoelectron Emission and Acoustic Emission", ASTM Special Technical Publication, American Society for Testing and Materials, pp. 143-157, Jan. 1, 1972.

* cited by examiner

*Primary Examiner* — Minh N Tang
(74) *Attorney, Agent, or Firm* — Jason K. Klindtworth

(57) ABSTRACT

An defect detection system includes an exoemission sensor having a conductive layer and an insulating layer. The exoemission sensor is mountable to a material of interest and configured to receive exoemissions from the material while in an atmosphere. The exoemission sensor outputs a signal based upon the received emissions. An analysis device is configured to receive the signal from the exoemission sensor and determine whether a defect is present in the material based upon the signal.

20 Claims, 4 Drawing Sheets

SYSTEMS AND METHODS FOR DEFECT DETECTION USING EXOELECTRONS

BACKGROUND OF THE INVENTION

The field of the present disclosure relates generally to analysis and monitoring of defects and fatigue in structures. More particularly, the present disclosure relates to systems and methods for fatigue detection utilizing exoelectron emission.

Typically, analysis and monitoring of defects and fatigue detection require that a physical crack or defect occur in the structure before a detection occurs. For example, techniques such as dye penetrants, acoustic, ultrasound, Eddy current and X-ray detection require that a physical crack or defect be present in a structure before such techniques allow for detection of a defect or fatigue in the structure. Such techniques thus do not allow for early detection of defects or fatigue before a defect or crack is already present.

Further, typically dye penetrating methods are very limited in resolution and accuracy, as cracks need to exist on the surface and be observable to the naked eye or under magnification to be detectable. Other techniques, such as acoustic, ultrasound and Eddy current X-ray techniques may provide higher resolution than dye penetrants, but the detection time can be long as multiple images must be analyzed and the costs can be high.

Exoemissions, as used herein, refers to the phenomenon of emission of charged particles (e.g., electrons) from solid surfaces after plastic deformation, stress, strain, abrasion or particle bombardment of the solid surface. Exoemissions are emitted at relatively low temperatures and at a rate that decreases with time. Typically, detection of exoelectrons has only been in systems under high vacuum (i.e., $<10^{-7}$ Torr) conditions, which has prevented exoelectron detection from being used for defect detection.

BRIEF DESCRIPTION OF THE INVENTION

In one aspect, a defect detection system includes an exoemission sensor having a conductive layer and an insulating layer. The exoemission sensor is mountable to a material of interest and configured to directly receive exoemissions from the material while in an atmosphere and electrically biased to the material of interest. The exoemission sensor outputs a signal based upon the received emissions. An analysis device is configured to receive the signal from the exoemission sensor and determine whether a defect is present in the material based upon the signal.

In another aspect a method of detecting a defect in a material in an atmosphere includes placing an exoemission sensor on the material in a test location and receiving exoemissions of the material by the sensor. The sensor outputs signals based upon received exoemissions. The method includes comparing a presently received signal to a previously received signal and determining whether a defect is present in the material based upon the comparison.

In yet another aspect, an in-atmosphere defect detection system includes at least one flexible exoemission sensor mountable to a material of interest. The exoemission sensor includes a conductive layer and a patterned insulating layer disposed on a surface of the conductive layer. The exoemission sensor is configured to output a signal based upon received exoemissions. The patterned layer is configured to maintain an electrical bias between the exoemission sensor and the material of interest and block exoemissions from reaching the surface of the conductive layer. An analysis device is in communication with the sensor and configured to determine whether a defect in the material exists based upon the received signals.

DETAILED DESCRIPTION OF THE INVENTION

Described herein are systems and methods for defect detection using exoemissions in atmospheric conditions. As used herein, atmospheric conditions means conditions not under vacuum and not exceeding typical atmospheric pressure ranges.

Figure 1:
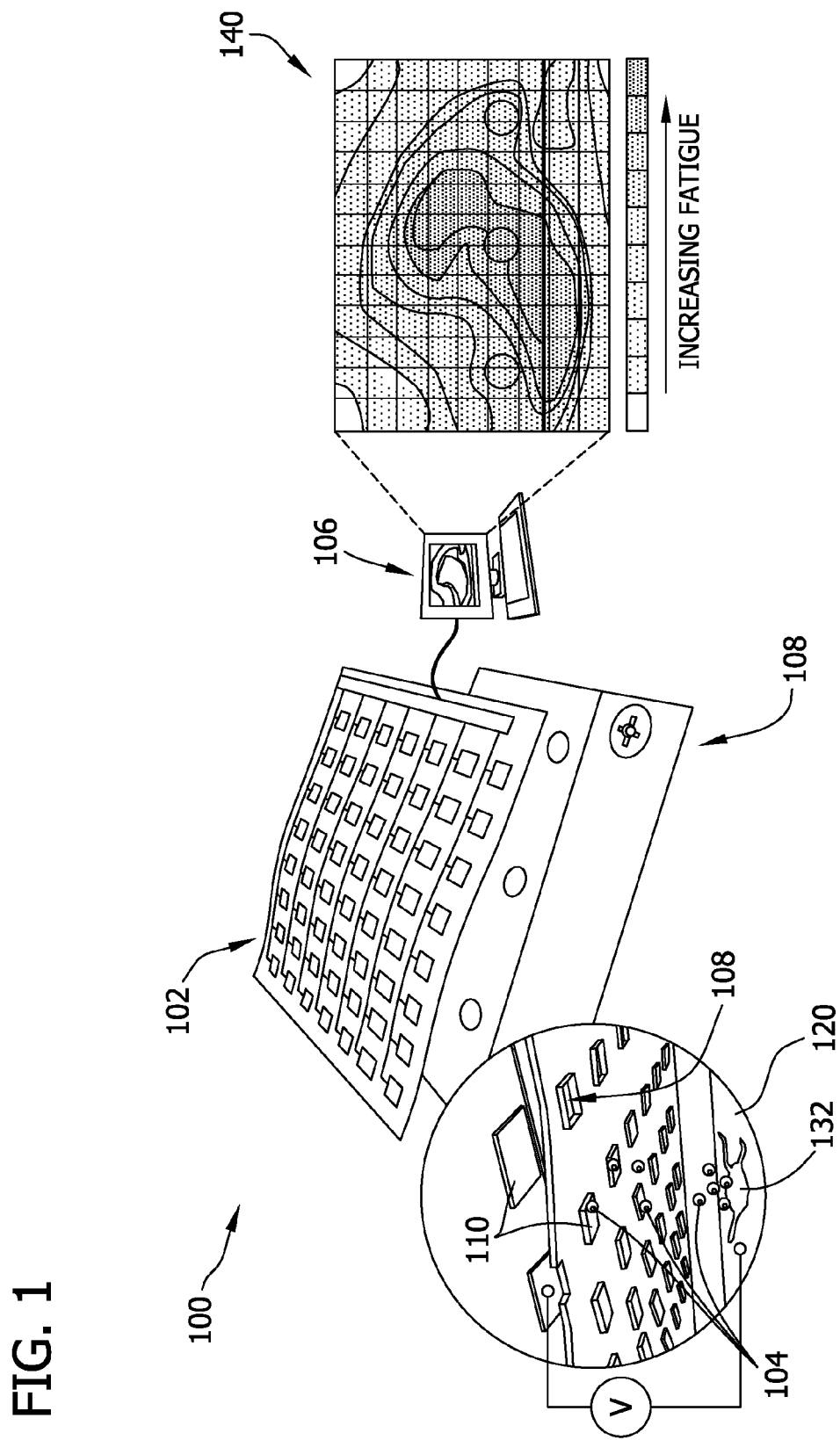
FIG. 1 shows an exemplary embodiment of a defect detection system according to the present disclosure.

FIG. 1 shows one embodiment of a defect detection system 100 that includes an exoemission sensor 102 configured to receive exoemissions 104 and an analysis device 106. Exoemission sensor 102 is mountable to a material of interest 108. In one embodiment, exoemission sensor 102 is flexible and able to conform to irregular shapes of material of interest 108. For example, in one embodiment, material of interest 108 is the skin of an aircraft, and exoemission sensor 102 is flexible to an extent that allows exoemission sensor 102 to conform to the shape of the aircraft skin.

Figure 2:
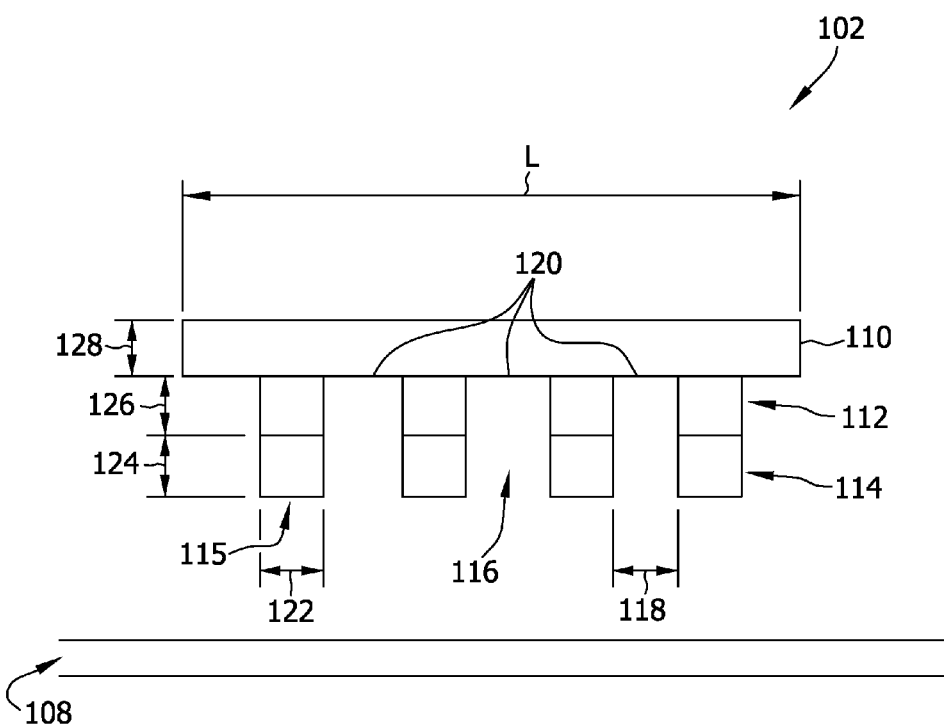
FIG. 2 shows a cross-section of an exemplary embodiment of an exoemission sensor of the present disclosure.

A cross-section of an exemplary exoemission sensor 102 is shown in FIG. 2. In one embodiment, exoemission sensor 102 includes a conductive layer 110, an adhesive layer 112 and an insulating layer 114. In one embodiment, conductive layer 110 is a highly conductive material such as copper, gold, silver and the like. In some embodiments, insulating layer 114 is made of a solid material such as a polyimide film, for example KAPTON®. In another embodiment, exoemission sensor 102 is formed of PYRALUX® manufactured by DuPont™. However, conductive layer 110 and insulating layer 114 may be formed of any material that allows the exoemission sensor to function as described herein.

Figure 3:
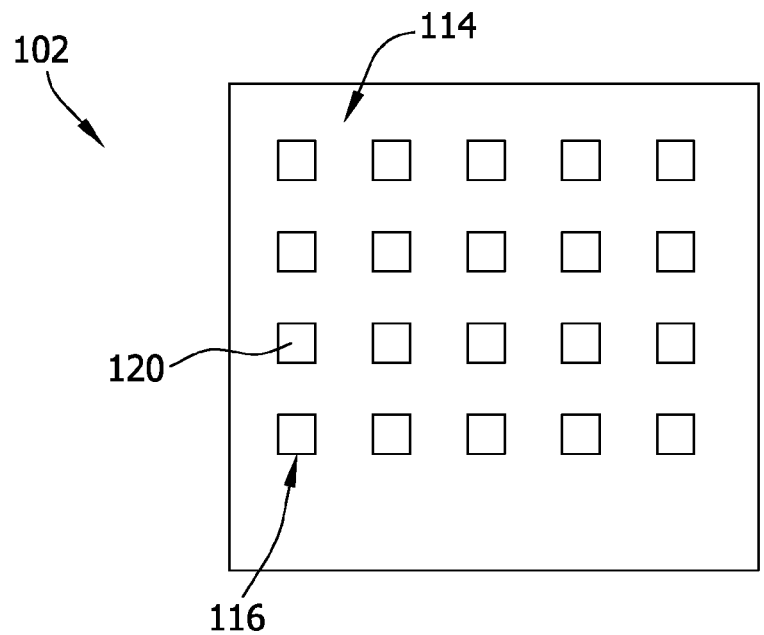
FIG. 3 shows a top view of an exemplary embodiment of the exoemission sensor of FIG. 2.
Figure 4:
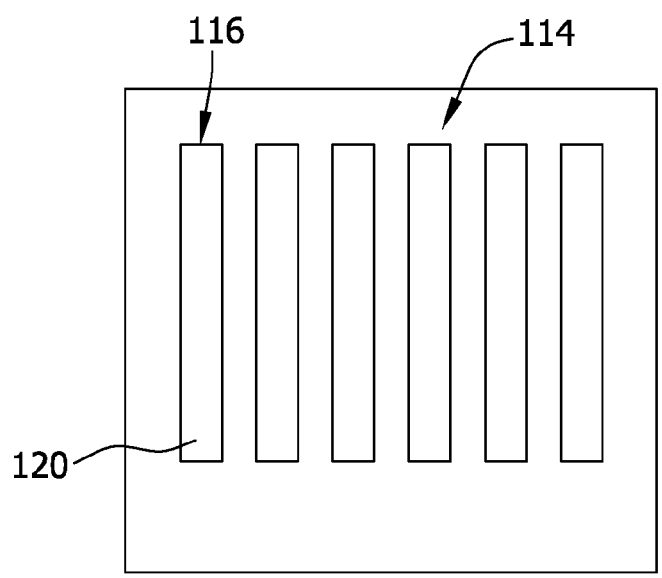
FIG. 4 shows a top view of another exemplary embodiment of the exoemission sensor of FIG. 2.

In one embodiment, adhesive layer 112 and insulating layer 114 are patterned on conductive layer 110 such that conductive layer 110 is exposed in a pattern. In one embodiment, as shown in FIG. 3, insulating layer 114 is removed in removed portions 116 to form a grid pattern exposing electrodes 120. In some embodiments, removed portions 116 are formed in shapes such as squares, circles, triangles and any other symmetric or non-symmetric shape. In another embodiment, as shown in FIG. 4, removed portions 116 are formed in parallel troughs. In some embodiments, removed portions 116 are formed in insulating layer 114 and/or adhesive layer 112 using laser ablation, chemical etching, mechanical etching or the like. Removed portion 116 has a width dimension 118 that ranges from about 50 micrometers to 150 micrometers. In one embodiment, width 118 is about 100 micrometers. Non-removed portions 115 of insulating layer 114 have a width dimension 122 that ranges from about 50 micrometers to 150 micrometers. In one embodiment, width 122 is about 100 micrometers. In one embodiment, dimensions of removed portions 116 and non-removed portions 115 are same, and in other embodiments dimensions of removed portions 116 and non-removed portions 115 are different from each other. Insulating layer 114 has a thickness 124 that ranges from about 10 micrometers to 20 micrometers. In one embodiment, thickness 124 is about 12 micrometers. Adhesive layer 112 has a thickness 126 that ranges from about 10 micrometers to 20 micrometers. In one embodiment, thickness 126 is about 12 micrometers. Conductive layer 110 has a thickness 128 that ranges from about 50 micrometers to 100 micrometers. In one embodiment, thickness 128 is about 75 micrometers. However, the thicknesses 124, 126 and 128 and width dimensions 120 and 122 may be any thickness/dimension that allows the exoemission sensor to function as described herein. Length L of exoemission sensor may be any suitable length for mounting on material of interest 108, ranging from several millimeters to several meters in length, depending on the application. In one embodiment, length L is about 10 millimeters to about 50 millimeters. In another embodiment, length L is 25 millimeters.

For atmospheric detection, the product of pressure (in units of Pascal) and the distance between electrodes (in meters) is kept below about 3 such that the equation pd<3 Pa-m (where p=pressure and d=distance between electrodes) is satisfied. The pressure is measured at atmospheric conditions when attaching exoemission sensor 102 to material of interest 108.

In operation, exoemission sensor 102 is mounted on material of interest 108. In one embodiment, exoemission sensor 102 is in direct contact with material of interest 108, with substantially no gap between exoemission sensor 102 and material of interest 108. In one embodiment, an adhesive material, such as an adhesive tape, is disposed over the top of exoemission sensor 102 and secures exoemission sensor 102 directly to material of interest 108 at a periphery of exoemission sensor 102. In another embodiment, a second adhesive is disposed between material of interest 108 and insulating layer 114 to adhere exoemission sensor 102 to material of interest 108. Exoemission sensor 102 is operatively connected to analysis device 106. When material of interest 108 undergoes plastic deformation, stress, strain, abrasion or particle bombardment, exoemissions 104 are emitted from the surface of material of interest 108. In use, exoemission sensor 102 receives exoemissions 104 at electrodes 120 through removed portions 116 when exoemission sensor 102 is electrically biased (i.e., voltage biased) with respect to material of interest 108. Insulating layer 114 substantially blocks exoemissions 104 from otherwise reaching conductive layer 110 outside of electrodes 120 and provides the insulating layer to support the electrical bias.

Figure 5:
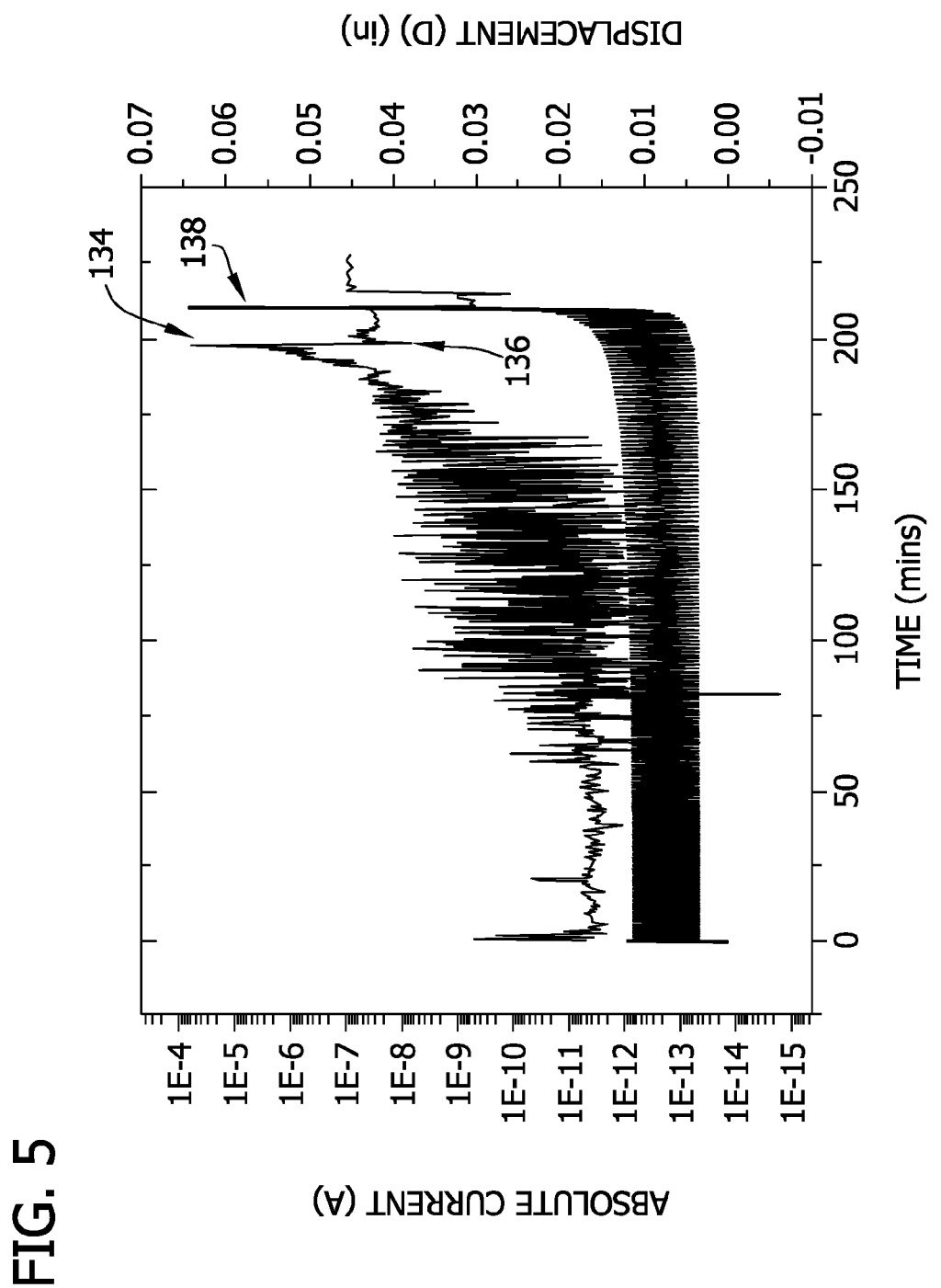
FIG. 5 shows an exemplary plot of a signal of an exoemission sensor of the present disclosure.

Upon receiving exoemissions 104, exoemission sensor 102 sends a signal, such as an electrical signal, to analysis device 106. Analysis device 106 receives the signal and determines whether a defect 132 is present in material of interest 108. In one embodiment, as shown in FIG. 5, analysis device 106 receives the signal and plots the signal as an absolute current (measured in amperes) on one axis and time on another axis. When the absolute current reaches a predetermined level, analysis device 106 indicates that a defect is present in material of interest 108. As shown in FIG. 5, an increase in absolute current A leads up to the initiation of a major defect, such as cracking. In one embodiment, analysis device 106 indicates that a defect in material of interest 108 is present when absolute current A reaches a peak value 134, which occurs before a local minimum value 136, which indicates the onset of cracking. The onset of cracking creates a local minimum value of absolute current A because the cracking relieves stress on the material of interest, thus reducing an amount of exoemissions received by the exoemission sensor at the time of cracking (i.e., increased stress may increase an amount of exoemissions, while reduced stress may reduce an amount of exoemissions from material of interest 108).

In one embodiment, analysis device 106 correlates the signal to a displacement D of material of interest 108 using a lookup table or simultaneous measurement of displacement D. For example, as shown in FIG. 5, displacement D reaches a peak value 138 at or near local minimum value 136, indicating a major defect, such as a crack, has occurred in material of interest 108. In another embodiment, analysis device compares a present received signal with a previously received signal, and determines a defect is present in the material based upon the comparison of the signals, such as when a predetermined difference between the compared signals is present (i.e., a difference between local minimum value 136 and peak value 134).

In another embodiment, analysis device 106 generates a fatigue map 140 showing a level of fatigue of the material in a plurality of locations based upon the received signals from exoemission sensor 102 corresponding to locations of electrodes 120.

In some embodiments, the above described systems and methods are electronically or computer controlled. The computer implemented embodiments described herein are not limited to any particular system controller or processor for performing the processing and tasks described herein. The term controller or processor, as used herein, is intended to denote any machine capable of performing the calculations, or computations, necessary to perform the tasks described herein. The terms controller and processor also are intended to denote any machine that is capable of accepting a structured input and of processing the input in accordance with prescribed rules to produce an output. It should also be noted that the phrase "configured to" as used herein means that the controller/processor is equipped with a combination of hardware and software for performing the tasks of embodiments of the invention, as will be understood by those skilled in the art. The term controller/processor, as used herein, refers to central processing units, microprocessors, microcontrollers, reduced instruction set circuits (RISC), application specific integrated circuits (ASIC), logic circuits, and any other circuit or processor capable of executing the functions described herein.

The embodiments described herein embrace one or more computer readable media, including non-transitory computer readable storage media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Aspects of the disclosure transform a general-purpose computer into a special-purpose computing device when configured to execute the instructions described herein. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

A computer or computing device such as described herein has one or more processors or processing units, system memory, and some form of computer readable media. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Combinations of any of the above are also included within the scope of computer readable media.

Technical effects of the present disclosure include one or more of providing the ability to detect a defect in a material of interest and generating a fatigue map showing a level of fatigue of the material in a plurality of locations based upon the received signals from an exoemission sensor for determining a location of a defect.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A defect detection system comprising:
    an exoemission sensor comprising a conductive layer and an insulating layer, the exoemission sensor mountable to a material of interest and configured to directly receive exoemissions from the material of interest, while in an atmosphere and electrically biased to the material of interest, and to output a signal based upon the received emissions; and
    an analysis device configured to receive the signal from the exoemission sensor and determine whether a defect is present in the material based upon the signal.

2. The defect detection system according to claim 1, wherein the exoemissions are exoelectrons.

3. The defect detection system according to claim 1, wherein the exoemission sensor comprises a flexible layer mountable to a surface of the material.

4. The defect detection system according to claim 1, wherein the exoemission sensor further comprises an adhesive layer intermediate to the conductive layer and the insulating layer and the adhesive layer has openings corresponding to openings in the insulating layer.

5. The defect detection system according to claim 4, wherein at least part of the insulating layer is configured to sustain an electrical bias between the exoemission sensor and the material of interest.

6. The defect detection system according to claim 4, wherein the insulating layer is patterned on a surface of the conductive layer.

7. The defect detection system according to claim 1, wherein:
    the insulating layer is patterned on a surface of the conductive layer, and
    the analysis device is configured to determine a location of the displacement of the material based upon the signal.

8. The defect detection system according to claim 1, wherein the analysis device compares a present received signal with a previously received signal, and determines a defect is present in the material based upon the comparison of the present and previously received signals.

9. The defect detection system according to claim 1, wherein the analysis device is configured to indicate a defect is present in the material at a predetermined level of exoelectron emission.

10. The defect detection system according to claim 1, wherein the exoemission sensor is configured to satisfy the equation pd<3 Pa-m, where p is equal to atmospheric pressure in units of Pascal and d is equal to a distance between electrodes of the exoemission sensor in units of meters.

11. A method of detecting a defect in a material in an atmosphere, comprising:
    placing an exoemission sensor on the material in a test location;
    electrically biasing the exoemission sensor to the material of interest;
    receiving exoemissions of the material by the sensor, the sensor outputting signals based upon received exoemissions;
    comparing a later received signal to a previously received signal;
    determining whether a defect is present in the material based upon the comparison.

12. The method according to claim 11, wherein the exoemissions are exoelectrons emitted from the material when the material is stressed.

13. The method according to claim 11, wherein the exoemission sensor comprises a flexible layer mountable to a surface of the material.

14. The method according to claim 11, wherein the exoemission sensor comprises a conductive layer and an insulating layer.

15. The defect detection system according to claim 14, wherein the insulating layer is configured to sustain an electrical bias between the exoemission sensor and the material of interest.

16. The method according to claim 14, wherein the insulating layer is patterned on a surface of the conductive layer.

17. The defect detection system according to claim 16, further comprising determining a location of the displacement of the material based upon the signals.

18. The defect detection system according to claim 11, wherein placing the exoemission sensor on the material in a test location and receiving the exoemissions are done in an atmosphere such that the equation pd<3 Pa-m, where p is equal to atmospheric pressure in units of Pascal and d is equal to a distance between electrodes of the exoemission sensor in units of meters, is satisfied.

19. An in-atmosphere defect detection system comprising:
    at least one flexible exoemission sensor mountable to a material of interest and comprising a conductive layer and a patterned insulating layer disposed on a surface of the conductive layer, the exoemission sensor configured to output signals based upon received exoemission;
    wherein the patterned layer is configured to maintain an electrical bias between the exoemission sensor and the material of interest; and an analysis device in communication with the sensor and configured to determine whether a defect in the material exists based upon the signals.

20. The in-atmosphere defect detection system according to claim 19, wherein the analysis device is configured to generate a fatigue map showing a level of fatigue of the material in a plurality of locations based upon the signals.

* * * * *

UNITED STATES PATENT AND TRADEMARK OFFICE
CERTIFICATE OF CORRECTION

PATENT NO. : 8,829,886 B2
APPLICATION NO. : 13/325731
DATED : September 9, 2014
INVENTOR(S) : Weaver et al.

Page 1 of 1

It is certified that error appears in the above-identified patent and that said Letters Patent is hereby corrected as shown below:

In the Claims

In Column 6, Line 64, in Claim 19, delete "exoemission;" and insert -- exoemissions; --, therefor.

Signed and Sealed this
Seventh Day of April, 2015

Michelle K. Lee
*Director of the United States Patent and Trademark Office*